United States Patent
Hammer

(10) Patent No.: US 9,770,396 B2
(45) Date of Patent: Sep. 26, 2017

(54) USE OF ACRYLOYLDIMETHYLTAURATE SALT/VINYL PYRROLIDONE (VP) COPOLYMERS IN THE PREPARATION OF WET WIPES

(71) Applicant: ALBAAD MASSUOT YITZHAK, LTD., M.P. SDE GAT (IL)

(72) Inventor: Ifat Hammer, Rehovot (IL)

(73) Assignee: ALBAAD MASSUOT YITZHAK, LTD., M.P. SDE GAT (IL)

( * ) Notice: Subject to any disclaimer, the term of this patent is extended or adjusted under 35 U.S.C. 154(b) by 175 days.

(21) Appl. No.: 14/721,085

(22) Filed: May 26, 2015

(65) Prior Publication Data

US 2015/0342862 A1 Dec. 3, 2015

(30) Foreign Application Priority Data

Jun. 2, 2014 (IL) .......................................... 232953

(51) Int. Cl.
| | | |
|---|---|---|
| *A61K 8/41* | (2006.01) | |
| *A61Q 19/00* | (2006.01) | |
| *A61Q 17/00* | (2006.01) | |
| *C08F 228/02* | (2006.01) | |
| *C08F 226/10* | (2006.01) | |
| *A61K 8/81* | (2006.01) | |
| *A61K 8/02* | (2006.01) | |

(52) U.S. Cl.
CPC ............ *A61K 8/416* (2013.01); *A61K 8/0208* (2013.01); *A61K 8/8182* (2013.01); *A61Q 17/005* (2013.01); *A61Q 19/00* (2013.01); *A61Q 19/007* (2013.01); *C08F 226/10* (2013.01); *C08F 228/02* (2013.01); *A61K 2800/48* (2013.01)

(58) Field of Classification Search
None
See application file for complete search history.

(56) References Cited

U.S. PATENT DOCUMENTS

| | | | | |
|---|---|---|---|---|
| 2004/0161435 A1* | 8/2004 | Gupta | .................. | A61K 8/0212 424/401 |
| 2005/0008681 A1* | 1/2005 | Deckner | .............. | A61K 8/0208 424/443 |
| 2012/0189675 A1* | 7/2012 | Matsuo | .................. | A61K 8/044 424/401 |
| 2013/0158130 A1* | 6/2013 | Heuer | .................... | A61K 8/731 514/772.1 |

FOREIGN PATENT DOCUMENTS

| | | |
|---|---|---|
| JP | 2013203678 A | 10/2013 |
| WO | 2009/125405 A2 | 10/2009 |
| WO | 2013/103056 A1 | 7/2013 |

OTHER PUBLICATIONS

European Search Report from counterpart foreign application (European patent application No. 15170036.6-1458) 7 pages, dated Sep. 28, 2015.
Anonymous: Essential Ingredients Product Search Results, Oct. 1, 2012, 1 page, XP55214514, retrieved from URL:http://www.essentialingredients.com/productdetailsingle.aspx?ItemNum=CL-ArstflxAVC-025-CT.
Artistoflex AVS Product Fact Sheet, May, 31, 2013, 3 pages—XP55214525; retreived from URL:http://www.essential ingredients.com/pdf/AristoflexAVS_PDS.pdf.

* cited by examiner

*Primary Examiner* — Robert A Wax
*Assistant Examiner* — Quanglong Truong
(74) *Attorney, Agent, or Firm* — Roach Brown McCarthy & Gruber, P.C.; Kevin D. McCarthy

(57) ABSTRACT

The invention provides novel liquid compositions comprising acryloyldimethyltaurate salt/VP copolymer, as well as wet wipe products including such compositions.

3 Claims, No Drawings

USE OF ACRYLOYLDIMETHYLTAURATE SALT/VINYL PYRROLIDONE (VP) COPOLYMERS IN THE PREPARATION OF WET WIPES

FIELD OF THE INVENTION

The invention relates to novel liquid compositions comprising acryloyldimethyltaurate salt/VP copolymer for use in wet wipe products, and to wet wipe products comprising said liquid composition. The present invention also relates to a method of producing the liquid composition of the invention.

BACKGROUND OF THE INVENTION

All publications mentioned throughout this application are fully incorporated herein by reference, including all references cited therein.

Disposable wet wipes or towelettes pre-moistened with a liquid or cream are well known in the art and are commonly used for personal care. Impregnated wet wipes typically consist of a dry fabric, usually a nonwoven fabric, which is made by any known technology of laying and bonding. Examples of such technologies include, but is not limited to, air-laid processes, wet-laid processes, hydroentangling processes, staple fiber carding and bonding, and solution spinning. The nonwoven fabric is then converted, cut, impregnated with liquid, folded, stacked in layers and packed as wet wipes.

The liquid in which the fabric is impregnated in is usually an aqueous composition combined with various ingredients such as humectants, emollients, surfactants, emulsifiers, anti-microbial agents, perfumes, pH adjusting agents, active ingredients, etc. Current converting technologies spray the liquid onto the nonwoven fabric via nozzles, which requires the liquids to have low viscosity of about 50 mPas and no more than 2000 mPas. This means that only low viscous impregnation liquids can be used, which limits the possible impregnation liquids and the usable ingredients therein.

While known wipe products can deliver beneficial ingredients onto the skin of the user, they do not provide the cosmetic, pleasant and esthetic sensation, which is achieved when using standard cosmetic creams, lotions and gels.

WO 2009/125405 discloses a wet wipe product in which viscosity of the anionic polysaccharides is formed in the presence of cations. These anionic polysaccharides are not compatible with cationic substances, and thus such preparations are limited in composition. For example, a cationic biocide such as Benzalkonium Chloride, is not compatible with Algin, and the incorporation of both may result in sedimentation. It is submitted that the polymer of the present invention is compatible with anions, cations and non-ionic substances.

SUMMARY OF THE INVENTION

The present invention relates to a wet wipe product comprising a fabric and a liquid composition comprising acryloyldimethyltaurate salt/VP copolymer for use in wet wipe products.

According to an embodiment of the invention, the acryloyldimethyltaurate salt is sodium acryloyldimethyltaurate.

In another embodiment of the invention, the wet wipe further comprises cationic biocides such as Benzalkonium Chloride and Chlorhexidine Digluconate.

In another embodiment of the invention, the wet wipe comprises a nonwoven fabric.

In another embodiment of the invention, the wet wipe comprises a sodium acryloyldimethyltaurate/VP copolymer.

In another embodiment of the invention, the nonwoven fabric comprises fibers selected from the group consisting of cellulose fibers, polyester fibers, polypropylene fibers, polylactic acid fibers and mixtures thereof.

In another aspect, the present invention relates to a liquid composition comprising acryloyldimethyltaurate salt/VP copolymer for use in wet wipe products.

In another embodiment of the invention, the acryloyldimethyltaurate salt is sodium acryloyldimethyltaurate.

In another embodiment of the invention, the composition further comprises cationic biocides such as Benzalkonium Chloride and Chlorhexidine Digluconate.

In another aspect, the invention relates to a method of producing the liquid composition, which comprises solubilizing the hydrophilic components in hot water; in parallel, mixing the oily phase with the emulsifiers, sodium acryloyldimethyltaurate/VP copolymer in a separate vessel and heating them using effective agitation; Homogenizing the two mixtures together under suitable conditions to cause formation of a homogeneous and stable emulsion; cooling the resulting mixture by adding cold water; optionally, adding skin conditioning agents, bactericides and fragrances; and adjusting the pH.

DETAILED DESCRIPTION OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. The materials and methods provided in the examples are illustrative only and are not intended to be limiting.

It is an object of the invention to provide thixotropic liquid compositions and wet wipes impregnated therewith useful for delivery of said compositions to the skin of the user. "Thixotropic", as used herein, encompass the rheological behavior of a pseudoplastic fluid having flow (viscosity) which is time-dependent. At constant applied shear rate, the viscosity of a thixotropic fluid gradually decreases.

The present invention provides novel liquid compositions comprising a acryloyldimethyltaurate salt/vinyl pyrrolidone (VP) copolymers as the active agent, and use thereof to form a wet wipe product, which cleans the skin while providing cosmetic treatment thereto. Accordingly, the wet wipes of the invention can apply the liquid compositions of the invention onto the skin, thereby providing the user with cosmetic benefits as well as silky and soft sensation.

Thus, in one aspect of the present invention, there is provided a wet wipe product comprising sodium acryloyldimethyltaurate/vinyl pyrrolidone (VP) copolymers as the active agent.

As used herein the term "liquid composition" should be understood to encompass a liquid, a solution, an aqueous dispersion, a gel, an emulsion, a water-in-oil emulsion, an oil-in-water emulsion, a paste, a lotion, etc.

Liquid compositions as used herein may comprise: water, a polysaccharide polymer and cations; or water and a polysaccharide polymer.

As used herein, the term "fabric" includes nonwoven- and woven-fabric, or any porous-fabric which is capable of holding the composition within the pores of the substrate.

As used herein, the term "nonwoven" fabric should be understood to encompass any nonwoven material or fabric. Non-limiting examples of nonwoven fabric are fabrics based on cellulose fibers, biopolymers such as, but not limited to polylactic acid, and synthetic polymeric fibers e.g. polyester and polypropylene, and combinations thereof. Nonwoven materials may include one or more layers of fibrous material, e.g. a laminate of fibrous material. The separate layers may be formed of similar or dissimilar materials, and may be bound together by any binder composition.

As used herein, the term "impregnate" encompasses the filling (saturating), partial or complete, of voids and interstices in a fabric with a compound or a composition, by any technique known in the art, such as, soaking, spraying, etc.

Thus, in one embodiment of the invention, the wet wipes of the invention are made from a nonwoven fabric. In one embodiment, the wet wipes of the invention may contain from about 150% wt. to about 450% wt. of the liquid compositions of the invention.

The term "wet wipe" as used herein should be understood to encompass a combination of a fabric and the liquid composition of the present invention, combined or pre-combined for later use. The term "disposable wet wipe" as used herein should be understood to encompass wipe products which are intended to be discarded after use, i.e. it is not intended to be laundered or reused, although it might be recycled or reused.

According to one embodiment, the wet wipes of the invention comprise a liquid composition or a cream.

The liquid composition of the invention is based on acryloyldimethyltaurate salt/vinyl pyrrolidone (VP) copolymers as the active agent. A non-limiting example of an acryloyldimethyltaurate salt is sodium acryloyldimethyltaurate.

Clinical trials involving the application of the liquid compositions of the invention onto the skin of test-subjects have shown that the liquid compositions of the invention are safe for use and have no side effects.

In a further aspect of the invention there is provided a method of producing the wet wipe of the invention comprising impregnating a fiber or fabric with the composition of the invention comprising acryloyldimethyltaurate salt/VP copolymers.

An example of a liquid composition which can be combined with or impregnated onto a fabric in order to produce the wet wipes of the invention is a liquid composition comprising sodium acryloyldimethyltaurate/VP copolymer.

According to one embodiment, the wet wipes of the invention further comprise at least one additional agent selected from the group consisting of an anti-microbial agent, a pH-adjusting agent, a chelating agent, a water-soluble polyol, a perfume ingredient, a powder, a humectant (moistener), a skin soothing aid, a plant extract, a cosmetic active ingredient, an emollient and a fragrance, and mixtures thereof.

Examples of cosmetic active ingredients suitable for use in the wet wipes of the invention are Tocopheryl Acetate, Alanine, Arginine, Allantoin, Caffeine, Ceramide, Collagen, Niacinamide, Ubiquinone, Retinyl Palmitate, Sphingolipids, etc.

Examples of acceptable skin soothing aids are acetyl cysteine, acetyl glutamine, alanine, ammonium caseinate, avena sativa, behenyl betaine, beta-glucan, bioflavanoids, bisabolol, caproyl salicylic acid, carnitine, ceramide-1, ceramide-2, ceramide-3, ceramide-4, ceramide-5, cetearyl phosphate, glycyrrhizic acid, lactoferrin, mineral salts, squalene, xanthan gum, etc.

Non-limiting examples of humectants are Sorbitol, Glycerin, Hexylene Glycol, Butylene Glycol, Pentylene Glycol, Ethylhexylglycerin, Panthenol, Glucose, Fructose, PEG-200, Urea, Caprylyl Glycol and so forth.

Non-limiting examples of emollients are oils, fats and lipids such as White Mineral Oil (Paraffinum Liquidum), Ethylhexyl Palmitate, and Caprylic/Capric Triglycerides, Caprylic/Capric Triglyceride, Cyclomethicone, Dimethicone, $C_{12-15}$ Alkyl Benzoate, Cetyl Esters, Palm Glycerides, Sucrose Oleate, Propylene Glycol Caprylate, Octadecane, Octyldodecanol, Oleyl Oleate, Myristyl Alcohol, Jojoba Esters, Ethylhexyl Isononanoate, 12-20 Isoparaffin, etc. Non-limiting examples of emulsifiers are Polyglycerol esters, Sucrose esters, fatty Alcohols, Phosphate esters, Sorbitan esters, etc.

In one embodiment, the composition may further contain one or more components selected from water-soluble polyols, pH-adjusting agents, anti-microbial agents and chelating agents.

Preservatives and anti-microbial agents improve shelf life of the liquid compositions of the invention and the wet wipes containing them. Therefore, in another embodiment of the invention, the liquid composition and the wet wipes of the invention may include such anti-microbial agents. Examples of such anti-microbial agents are parabens and their salts, Methylisothiazolinone, Ethylhexylglycerin, Organic Acids and their salts such as Sorbic Acid, Dehydroacetic Acid, Benzoic Acid, etc.

Biocides can further provide treatment properties to the preparation by helping reduce microorganisms on the skin. Non limiting examples of biocides as used in the invention include but are not limited to: Benzalkonium Chloride, Ethanol, Povidone Iodine, Chlorhexidine Diglucon and Isopropyl Alcohol.

Nonwoven fabrics suitable for the wet wipes of the invention can be manufacture according to any method known in the art. Such methods include web-laying; bonding; drying; and conversion. Nonwoven fabrics may be air-laid, wet-laid, spun-laid, melt blown, or carded. Nonwoven materials may be treated, for example, to join fibers of the nonwoven material or to enhance the strength of the nonwoven material. Such treatment may involve hydroentanglement, thermal bonding, or treatment with a binder.

The liquid composition of the invention may be prepared by any known method. Examples of such methods include, but is not limited to, oil-in-water and water-in-oil emulsion techniques. Usually, a process involves solubilizing the different hydrophilic components in hot water, or, under high shear forces. In parallel, mixing the hydrophobic components in a separate vessel and heating them. Thereafter, the two mixtures are mixed together under suitable conditions to cause formation of a homogeneous and stable emulsion. The mix is then cooled, e.g. by the addition of cold water. Afterwards, additional components are admixed, such as additional emulsifiers, bactericides, fragrances, etc., and the pH is adjusted. The final composition remains stable and homogeneous over time based upon the required shelf life of the composition and wet wipes containing it.

In one embodiment, such a mixture may be formed in one step by addition and mixing of each of the ingredients. In another embodiment, less than all of the ingredients may be pre-combined for subsequent combination with other ingredients or other pre-combined ingredients to form the mixture.

EXAMPLES

The following examples are set forth to further illustrate the present invention. The below examples, however, should not be construed in any way as limiting the present invention in any manner. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Preparation Example 1

The liquid composition of the invention is prepared by:
Heating 30% of the water to 80° C.;
Heating (in parallel) in a separate vessel the following mixture to 80° C.: Glyceryl Stearate+PEG-100 Stearate, Stearyl Alcohol, Paraffinum liquidum, dimethicone and Sodium Acryloyldimethyltaurate/VP Copolymer;
Adding the oily phase into the water, and homogenizing both mixtures for 20 minutes;
Cooling the mixture, while adding the rest of the cold water;
Adding one by one the following ingredients: Caprylyl/Capryl Glucoside, Phenoxyethanol, Ethylhexylglycerin, Fragrance, and homogenizing for 15 minutes;
Adding Benzalkonium chloride and Tetrasodium EDTA and mixing for another 15 minutes; and
Adjusting the pH with citric acid or sodium hydroxide as required.

Preparation Example 2

The liquid composition of the invention is prepared by:
Heating 30% of the water to 80° C.;
Heating (in parallel) in a separate vessel the following mixture to 80° C.: C14-22 Alcohols, C12-20 Alkyl Glucoside, Cetyl Alcohol, Dimethicone, Disodium Cocoamphodiacetate, Glycerin and Sodium Acryloyldimethyltaurate/VP Copolymer;
Adding the oily phase into the water, and homogenizing both mixtures for 20 minutes.
Cooling down the mixture, while adding the rest of the cold water
Adding one by one the following ingredients: Tetrasodium EDTA, Phenoxyethanol, Ethylhexylglycerin, Glycine Soja (Soybean) Oil, Tocopheryl Acetate, and homogenizing for 15 minutes; and
Adjusting the pH with citric acid or sodium hydroxide as required.

Example 3

| Ingredients (INCI Name) | % Active |
| --- | --- |
| Water (Aqua) | 86.043 |
| Mineral Oil (Paraffinum Liquidum) | 6.0000 |
| Dimethicone | 4.0000 |
| Glycerin | 1.0000 |
| Glyceryl Stearate PEG-100 Stearate | 1.0000 |
| Phenoxyethanol | 0.5000 |
| Sodium Acryloyldimethyltaurate/VP Copolymer | 0.4500 |
| Fragrance | 0.1000 |
| Stearyl Alcohol | 0.3000 |
| Ethylhexylglycerin | 0.2000 |
| Caprylyl/Capryl Glucoside | 0.1270 |
| Benzalkonium Chloride | 0.1000 |
| Tocopheryl Acetate | 0.1000 |
| Tetrasodium EDTA | 0.0400 |
| Sodium Hydroxide | 0.0400 |

Cream Preparation:
Heating 30% of the water to 80° C.;
Heating (in parallel) in a separate vessel the following mixture to 80° C.: Glyceryl Stearate+PEG-100 Stearate, Stearyl Alcohol, Paraffinum liquidum, dimethicone and Sodium Acryloyldimethyltaurate/VP Copolymer;
Adding the oily phase into the water, and homogenizing both mixtures for 20 minutes;
Cooling the mixture, while adding the rest of the cold water to reach temperatures below 35° C.;
Adding the following ingredients one by one: Caprylyl/Capryl Glucoside, Phenoxyethanol, Ethylhexylglycerin, Fragrance, and homogenizing for 15 minutes;
Adding Benzalkonium chloride and Tetrasodium EDTA and mixing for another 15 minutes; and
Adjusting the pH with citric acid or sodium hydroxide as required to reach a pH of 4.5-6.5.

Example 4

| Ingredients (INCI Name) | % Active |
| --- | --- |
| Water | q.s |
| Dimethicone | 3.200 |
| Glycerin | 1.250 |
| C14-22 Alcohols | 1.200 |
| C12-20 Alkyl Glucoside Parfum | 0.650 |
| Algae Extract | 0.333 |
| Cetyl Alcohol | 0.1000 |
| *Glycine Soja* (Soybean) Oil | 0.0010 |
| Tocopheryl Acetate | 0.1000 |
| Ethylhexylglycerin | 0.2000 |
| Phenoxyethanol | 0.7000 |
| Tetrasodium EDTA | 0.0168 |
| Disodium Cocoamphodiacetate | 0.3200 |
| Sodium Acryloyldimethyltaurate/VP Copolymer | 0.2000 |
| Sodium Hydroxide | q.s |
| Citric Acid | q.s |

Cream Preparation:
Heating 30% of the water to 80° C.;
Heating (in parallel) in a separate vessel the following mixture to 80° C.: C14-22 Alcohols, C12-20 Alkyl Glucoside, Cetyl Alcohol, Dimethicone, Disodium Cocoamphodiacetate, Glycerin and Sodium Acryloyldimethyltaurate/VP Copolymer;
Adding the oily phase into the water, and homogenizing both mixtures for 20 minutes.
Cooling down the mixture, while adding the rest of the cold water
Adding one by one the following ingredients: Tetrasodium EDTA, Phenoxyethanol, Ethylhexylglycerin, Glycine Soja (Soybean) Oil, Tocopheryl Acetate, and homogenizing for 15 minutes; and
Adjusting the pH with citric acid or sodium hydroxide as required.

Example 5

| Ingredients (INCI Name) | % Active |
| --- | --- |
| Water | q.s |
| Ethylhexyl Palmitate | 7.000 |
| Glycerin | 1.250 |
| C14-22 Alcohols | 1.200 |
| C12-20 Alkyl Glucoside | |
| Parfum | 0.650 |
| Cetyl Alcohol | 0.100 |
| Tocopheryl Acetate | 0.100 |
| Ethylhexylglycerin | 0.200 |
| Phenoxyethanol | 0.700 |
| Sodium Acryloyldimethyltaurate/VP Copolymer | 0.2000 |
| Disodium Cocoamphodiacetate | 0.320 |

Cream Preparation:
  Heating 30% of the water to 80° C.;
  Heating (in parallel) in a separate vessel the following mixture to 80° C.: C14-22 Alcohols, C12-20 Alkyl Glucoside, Cetyl Alcohol, Ethylhexyl Palmitate, Disodium Cocoamphodiacetate, Glycerin and Sodium Acryloyldimethyltaurate/VP Copolymer;
  Adding the oily phase into the water, and homogenizing both mixtures for 20 minutes;
  Cooling down the mixture, while adding the rest of the cold water;
  Adding one by one the following ingredients: Tetrasodium EDTA, Phenoxyethanol, Ethylhexylglycerin and Tocopheryl Acetate, and homogenizing for 15 minutes; and
  Adjusting the pH with citric acid or sodium hydroxide as required.

All methods described herein can be performed in any suitable order unless otherwise indicated herein or otherwise clearly contradicted by context. While the present invention has been described above in connection with the certain illustrative embodiments, it is to be understood that other similar embodiments may be used or modifications and additions may be made to the described embodiments for performing the same function of the present invention without deviating therefrom. Furthermore, all embodiments disclosed are not necessarily in the alternative, as various embodiments of the invention may be combined to provide the desired characteristics. Variations can be made by one having ordinary skill in the art without departing from the spirit and scope of the invention. Therefore, the present invention should not be limited to any single illustrative embodiment, but rather construed in breadth and scope in accordance with the recitation of the attached claims.

The invention claimed is:

1. A wet wipe product comprising
   i) a nonwoven fabric, and
   ii) a liquid composition comprising sodium acryloyldimethyltaurate vinyl pyrrolidone (VP) copolymer and a biocide selected from benzalkonium chloride and chlorhexidine digluconate, wherein said liquid composition is in an amount of from 150% wt to 450% wt relatively to said fibers.

2. The wet wipe of claim 1, wherein the nonwoven fabric comprises fibers selected from the group consisting of cellulose fibers, polyester fibers, polypropylene fibers, polylactic acid fibers, and mixtures thereof.

3. A method of producing the wipe of claim 1, comprising:
   solubilizing hydrophilic components including a biocide selected from benzalkonium chloride and chlorhexidine digluconate in hot water;
   mixing oily components including sodium acryloyldimethyltaurate/VP copolymer and heating them using effective agitation;
   homogenizing the two mixtures together under suitable conditions to cause formation of a homogeneous and stable emulsion;
   cooling the resulting mixture by adding cold water, thereby obtaining a liquid composition; and
   impregnating a fiber selected from the group consisting of cellulose fibers, polyester fibers, polypropylene fibers, polylactic acid fibers, and mixtures thereof, or a nonwoven fabric comprising said fiber, with said liquid composition in an amount of from 150% wt to 450% wt relatively to said fibers.

* * * * *